United States Patent
Leanna et al.

(10) Patent No.: US 9,642,624 B2
(45) Date of Patent: May 9, 2017

(54) DEVICES AND METHODS FOR LUMEN OCCLUSION

(71) Applicant: Boston Scientific Scimed, Inc., Maple Grove, MN (US)

(72) Inventors: Gary J. Leanna, Holden, MA (US); Paul Smith, Smithfield, RI (US); Sean P. Fleury, Brighton, MA (US); Man Minh Nguyen, Harvard, MA (US); Jason Weiner, Grafton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 152 days.

(21) Appl. No.: 14/664,183

(22) Filed: Mar. 20, 2015

(65) Prior Publication Data

US 2015/0265283 A1 Sep. 24, 2015

Related U.S. Application Data

(60) Provisional application No. 61/968,856, filed on Mar. 21, 2014.

(51) Int. Cl.
*A61B 17/12* (2006.01)
*A61B 18/14* (2006.01)
(Continued)

(52) U.S. Cl.
CPC ...... *A61B 17/12104* (2013.01); *A61B 17/068* (2013.01); *A61B 17/0643* (2013.01);
(Continued)

(58) Field of Classification Search
CPC ........ A61B 17/12027; A61B 17/12104; A61B 17/1203; A61B 17/12131; A61B 17/1214; A61B 17/12154
See application file for complete search history.

(56) References Cited

U.S. PATENT DOCUMENTS

| 7,913,698 B2 | 3/2011 | Barry et al. |
| 2003/0158563 A1 | 8/2003 | McClellan et al. |
| 2005/0081862 A1 | 4/2005 | Callister et al. |

FOREIGN PATENT DOCUMENTS

| EP | 1 512 383 A2 | 3/2005 | |
| JP | WO 2013133182 A1 * | 9/2013 | ............. A61B 17/24 |
| WO | WO 2013/133182 A1 | 9/2013 | |

OTHER PUBLICATIONS

Shah et al., "Design of the exhale airway stents for emphysema (EASE) trial: an endoscopic procedure for reducing hyperinflation", Jan. 7, 2011, vol. 11, No. 1, BMC Pulmonary Medicine (8 pages).
(Continued)

*Primary Examiner* — Thomas J Sweet
*Assistant Examiner* — Daniel Bissing
(74) *Attorney, Agent, or Firm* — Bookoff McAndrews, PLLC

(57) ABSTRACT

Methods and devices for at least partially occluding an airway of a lung is disclosed. The method includes deploying a catheter into the airway such that a balloon at a distal end of the catheter is positioned proximate a tissue wall that defines the airway, and inflating the balloon to cause pressure to be applied on a portion of the tissue wall. The method may also include deflating the balloon to cause the portion of the tissue wall to be drawn radially inward to at least partially occlude the airway.

18 Claims, 9 Drawing Sheets

(51) Int. Cl.
　　　A61F 2/04　　　　(2013.01)
　　　A61F 2/844　　　 (2013.01)
　　　A61M 25/10　　　 (2013.01)
　　　A61B 17/068　　　(2006.01)
　　　A61B 18/00　　　 (2006.01)
　　　A61F 2/848　　　 (2013.01)
　　　A61F 2/958　　　 (2013.01)
　　　A61B 17/00　　　 (2006.01)
　　　A61B 17/064　　　(2006.01)
　　　A61B 17/30　　　 (2006.01)
(52) U.S. Cl.
　　　CPC .. *A61B 17/12036* (2013.01); *A61B 17/12136* (2013.01); *A61B 17/12172* (2013.01); *A61B 17/12177* (2013.01); *A61B 18/1492* (2013.01); *A61F 2/04* (2013.01); *A61F 2/844* (2013.01); *A61M 25/10* (2013.01); *A61B 2017/00349* (2013.01); *A61B 2017/00557* (2013.01); *A61B 2017/00951* (2013.01); *A61B 2017/0647* (2013.01); *A61B 2017/12054* (2013.01); *A61B 2017/306* (2013.01); *A61B 2018/00541* (2013.01); *A61F 2/958* (2013.01); *A61F 2002/043* (2013.01); *A61F 2002/8483* (2013.01)

(56) References Cited

OTHER PUBLICATIONS

Herth et al., "Characterization of outcomes 1 year after endoscopic thermal vapor ablation for patients with heterogeneous emphysema", International Journal of COPD, 2012, pp. 397-405, vol. 7, Dove Medical Press Ltd. (9 pages).

Worcestor, Sharon, "Lung-Volume Reduction Coils Boost Walk Distance", Nov. 1, 2012, American College of Surgeons: ACS Surgery News, International Medical News Group, LLC (2 pages).

Zaid et al., "6 and 12 month outcomes following RePneu bronchoscopic lung volume reduction coil treatment", 2013, European Respiratory Society: Annual Congress 2013 (1 page).

Falkenstern-Ge et al., "Treatment of Severe Advanced Emphysema With Lung Volume Reduction Using Lung Sealant: A Case Report of 2 Patients", Jan. 2013, pp. 58-62, vol. 20, No. 1, Journal of Bronchology & Interventional Pulmonology (5 pages).

Venuta et al., "One-Way Valves for Bronchoscopic Lung Volume Reduction", Jun. 15, 2008, The Cardiothoracic Surgery Network, accessed Mar. 28, 2015, <http://www.ctsnet.org/print/portals/thoracic/newtechnology/article-3> (5 pages).

Springmeyer et al., "Development of a Bronchial Valve for Treatment of Severe Emphysema", Apr. 8, 2008, The Cardiothoracic Surgery Network, accessed Mar. 28, 2015, <http://www.ctsnet.org/print/portals/thoracic/newtechnology/article-10> (7 pages).

Galluccio et al., "Bronchoscopic lung volume reduction for pulmonary emphysema: preliminary experience with a new NOVATECH® endobronchial silicone one-way valve", 2010, pp. 213-215, Interactive Cardiovascular and Thoracic Surgery, European Association for Cardio-Thoracic Surgery (3 pages).

Watanabe et al., "Bronchial Occlusion With Endobronchial Watanabe Spigot", Oct. 2003, pp. 264-267, vol. 10, No. 4, Journal of Bronchology & Interventional Pulmonology (4 pages).

* cited by examiner

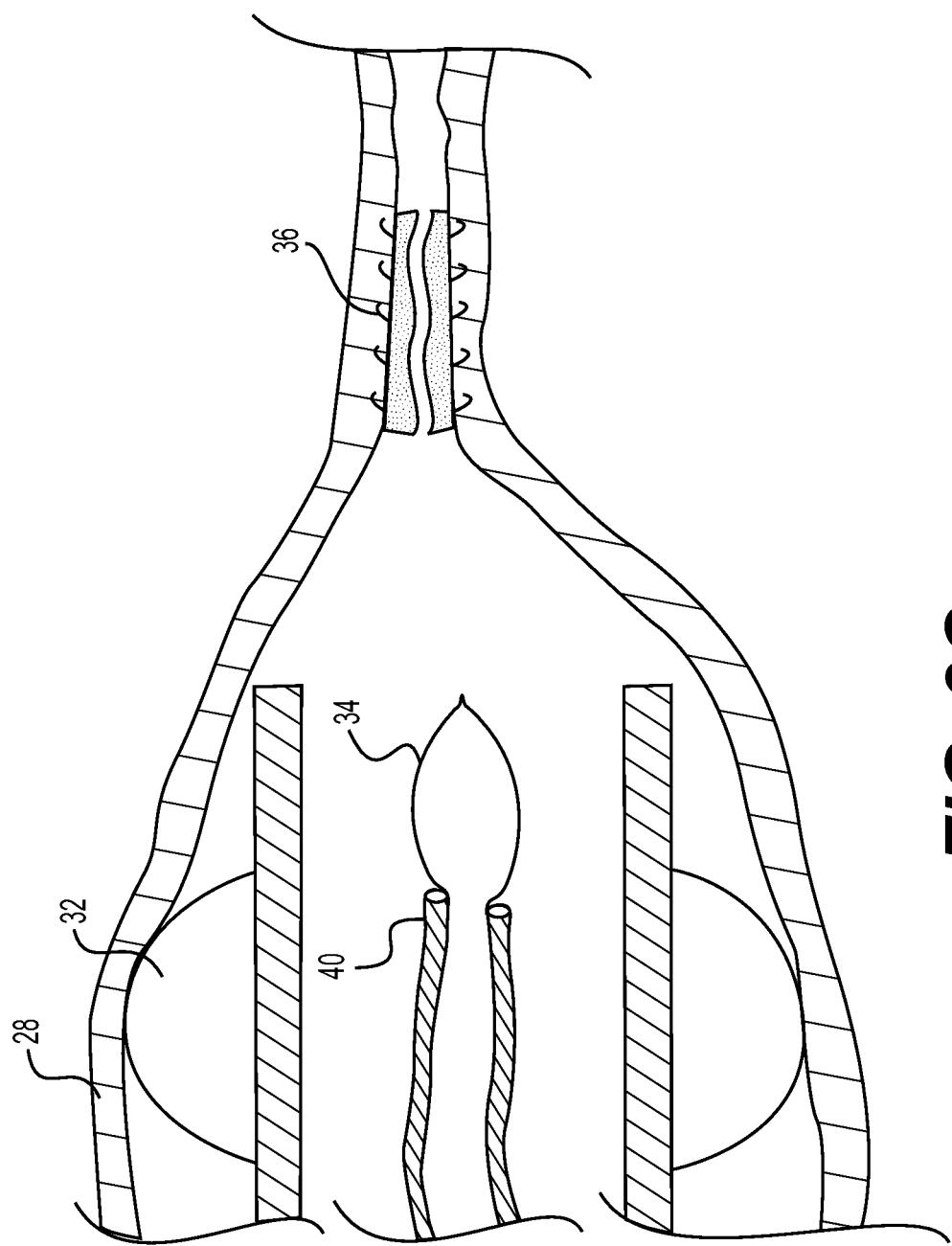

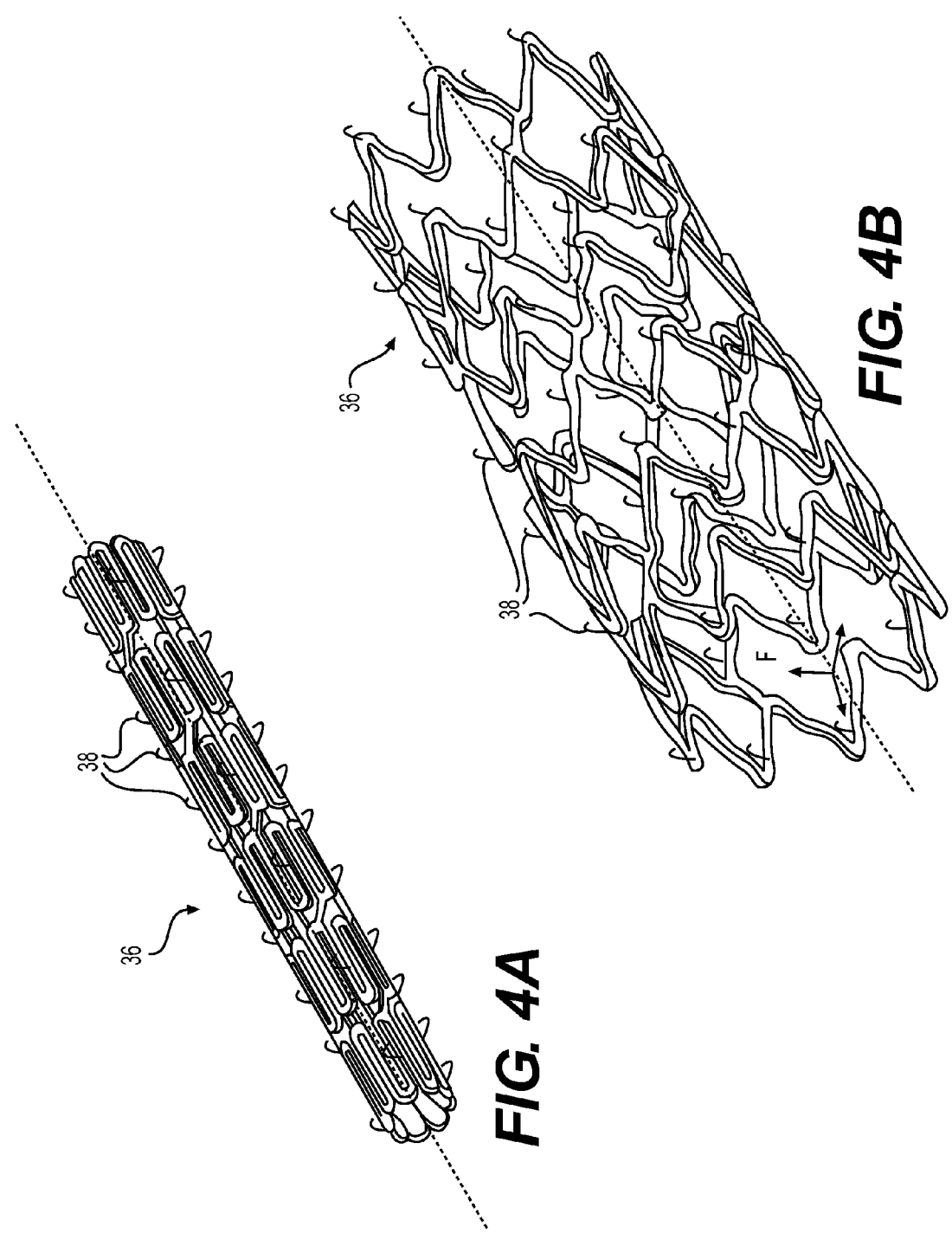

DEVICES AND METHODS FOR LUMEN OCCLUSION

CROSS-REFERENCE TO RELATED APPLICATION

This patent application claims benefit of priority under 35 U.S.C. §119 to U.S. Provisional Patent Application No. 61/968,856, filed Mar. 21, 2014, the entirety of which is incorporated herein by reference.

TECHNICAL FIELD

Embodiments of this disclosure relate to methods and devices for treating a lung, and more particularly, to devices and methods for lung volume reduction or isolation. The devices and methods disclosed herein, however, may be used to at least partially occlude or close a lumen or other opening in a patient.

BACKGROUND

Chronic obstructive pulmonary disease (COPD) is a serious progressive lung disease which makes it harder to breath. It currently affects over fifteen million people in the United States alone and is currently a leading cause of death in the country. The overwhelming primary cause of COPD is inhalation of cigarette smoke, responsible for over 90% of COPD cases. The economic and social burden of the disease is both substantial and increasing.

FIG. 1 depicts a healthy set of lungs 10 in an individual. A windpipe or trachea 12 connects the nose (not shown) and mouth (not shown) to the lungs 10. As air flows in through the nose and mouth of an individual, the trachea 12 transports the air to the lungs 10 for respiratory functions. The trachea 12 divides into the left 14 and right 16 bronchus stems, which further divide into a plurality of bronchi 18, bronchioles 20, and eventually, terminate in a plurality of alveoli 22. The alveoli 22 are small air sacs which enable gas exchange with the individual's blood stream. That is, they permit oxygen diffusion into the blood stream, and receive and expel $CO_2$ during exhalation.

COPD includes emphysema. As shown in FIG. 2A, emphysema may be characterized by the destruction of lung parenchyma 24, the functioning parts of the lungs 10. The parenchyma 24 includes the alveoli 22 walls, bronchioles 20, and the bronchi 18. Destruction of these tissues results in progressively increasing shortness of breath called dyspnea. As it worsens, emphysema turns the healthy alveoli 22, clustered like bunches of grapes, into large, irregular pockets with gaping holes in their inner walls, as shown in FIG. 2B. This reduces the surface area of the lungs and, in turn, the amount of oxygen that reaches an individual's blood stream.

Emphysema also slowly destroys the elastic fibers or tethers that hold open the airways, including the bronchioles 20 and bronchi 18, leading to the alveoli 22. This destruction may cause airways to reduce in diameter or collapse when one breaths out, which prevents the air in your lungs, including $CO_2$, from escaping during exhalation. A significantly reduced diameter airway 26 is depicted in FIG. 2B. A failure to exhale may result in hypercapnia, high blood gas levels of $CO_2$. Hypercapnia can lead to acidosis (lowering of pH levels), which is correlated to a significantly greater risk of mortality in COPD patients.

Treatment may slow progression of emphysema, but it cannot reverse any damage already sustained. In some cases, surgery may be required for treatment of emphysema. Surgery may include lung volume reduction (LVR) surgery, which removes or otherwise decreases damaged tissue in order to assist remaining, healthy tissue to function more efficiently. In severe cases, lung transplant surgery may be necessary.

SUMMARY

Embodiments of the present disclosure relate to, among other things, devices and methods for the treatment of diseased tissue, including tissue suffering from COPD or any other lung diseases or symptoms, via lung volume reduction or isolation. Each of the embodiments disclosed herein may include one or more of the features described in connection with any of the other disclosed embodiments.

In one embodiment, a method of at least partially occluding an airway of a lung is disclosed. The method includes deploying a catheter into the airway such that a balloon at a distal end of the catheter is positioned proximate a tissue wall that defines the airway. The method may also include inflating the balloon to cause pressure to be applied on a portion of the tissue wall. The method may further include deflating the balloon to cause the portion of the tissue wall to be drawn radially inward to at least partially occlude the airway.

This disclosed embodiment may include one or more of the following features. Inflating the balloon may cause an external surface of the balloon to adhere to the portion of the tissue wall; the method may further include detaching the balloon from the catheter to leave the balloon adhered to the portion of the tissue wall; the catheter may include a stent circumferentially disposed about the balloon, the stent may be configured to radially expand from a first unexpanded configuration to a second expanded configuration when the balloon inflates; inflating the balloon may cause the stent to anchor to the portion of the tissue wall; and deflating the balloon may cause the stent to separate from the balloon and transform to a less expanded configuration.

In another embodiment, a method of at least partially occluding an airway of a lung is disclosed. The method includes extending a tool into the airway through a sheath. The method may also include capturing at least a portion of a tissue wall of the airway using the tool, and retracting the tool into the sheath along with the captured portion of the tissue wall. Retracting the tool may gather the captured portion of the tissue together to at least partially occlude the airway.

The disclosed embodiment may include one or more of the following features. The method may further include applying a mechanical treatment or applying an energy treatment to the gathered portion of the tissue; applying a mechanical treatment may include one of applying an adhesive, a suture, or a tissue fastening device on the gathered portion of the tissue; the gathered portion of the tissue may form tissue folds, and applying an energy treatment may include applying electrical or ultrasonic energy on the tissue folds.

In another embodiment, a lung treatment system is disclosed. The system includes a catheter configured to be introduced into an airway of the lung. The airway may be defined by a tissue wall. The system may include an inflatable balloon fluidly or pneumatically coupled to a distal end of the catheter. The balloon may be configured to inflate in the airway to an inflated configuration. The inflated configuration may be a configuration in which the balloon causes pressure to be applied on a portion of the tissue wall. The balloon may also be configured to deflate from the inflated configuration to a deflated configuration so that the portion of the tissue wall is drawn radially inwards to at least partially occlude the airway.

The disclosed embodiment may include one or more of the following features. An external surface of the balloon may be configured to directly press against the portion of the tissue wall when the balloon is in the inflated configuration; the external surface of the balloon includes an adhesive configured to adhere to the portion of the tissue wall, and the balloon is configured to draw the portion of the tissue wall radially inwards when the balloon deflates; the system may further include a stent disposed about the balloon, the stent may be configured to radially expand from a first unexpanded configuration to a second expanded configuration when the balloon inflates; the stent may be configured to press directly against the portion of the tissue wall when the balloon is in the inflated configuration; the stent may include features configured to anchor to the portion of the tissue wall; the stent may include hooks configured to grasp the portion of the tissue wall; the stent may be configured to separate from the balloon when the balloon deflates; the stent may be configured to transform from the expanded configuration to a less expanded configuration separate from the balloon.

In another embodiment, a lung treatment system is disclosed. The system may include a sheath configured to extend into an airway of the lung. The airway may be defined by a tissue wall. The system may also include a tool configured to extend out of the sheath into the airway. The tool may be configured to capture at least a portion of the tissue wall, and retract into the sheath along with the captured portion of the tissue wall. The tool may include, without limitation, a hook, forceps shaped grasper, a snare, etc. Retracting the tool may gather the captured portion of the tissue together to at least partially occlude the airway.

This disclosed embodiment may include one or more of the following features. A tool may include an elongate member extending along a longitudinal axis and a plurality of prongs at a distal end of the elongate member, the plurality of prongs may be configured to transition between (a) a first unextended configuration in which the plurality of prongs extend substantially along the longitudinal axis, and (b) a second extended configuration in which the plurality of prongs extend at an angle to the elongate member, wherein the tool is configured to grasp at least a portion of the tissue wall in the extended configuration; the gathered portion of the tissue may form tissue folds; the system may also include a deployment device configured to be introduced into the airway to apply a mechanical or an energy treatment on the tissue folds; and wherein the mechanical or energy treatment includes one of cauterizing the tissue folds, applying sutures to the tissue folds, applying an adhesive on the tissue folds, or applying a tissue fastening device on the tissue folds.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 3A-3C illustrate the use of an exemplary embodiment of a disclosed device to occlude an airway in the lungs of FIG. 2B;

FIGS. 4A and 4B illustrate an exemplary embodiment of a device that may be used to occlude an airway in the lungs of FIG. 2B;

DETAILED DESCRIPTION

Overview

The present disclosure is drawn to devices and methods of treatment of diseased tissue. Such diseased tissue may suffer from COPD or any other lung disease, ailment, or symptom. Exemplary embodiments are drawn to devices and methods for lung volume reduction (LVR). LVR is a treatment in which diseased portions of the lungs are damaged, or otherwise removed or isolated from functioning, to enable healthy tissue to operate more efficiently. That is, inhaled air is prevented from reaching diseased tissue, allowing the remaining healthy tissue to more readily perform gas exchange. For example, one or more airways of a lung may be closed off or occluded to prevent normal respiratory functions therein. As air is no longer received within the closed off airway, the airway is starved and caused to die. As such, remaining healthy tissues are enabled to receive more air (e.g., the air that once was directed to the now occluded airway). Therefore, a lung 10 may perform respiratory functions more efficiently. While principles of the present disclosure are described herein with reference to treatments for the lungs of a patient, it should be understood that the disclosure is not limited thereto. Rather, the devices and methods may find applicability to occlude any luminal tissue structure.

Exemplary Embodiments

Figure 1:
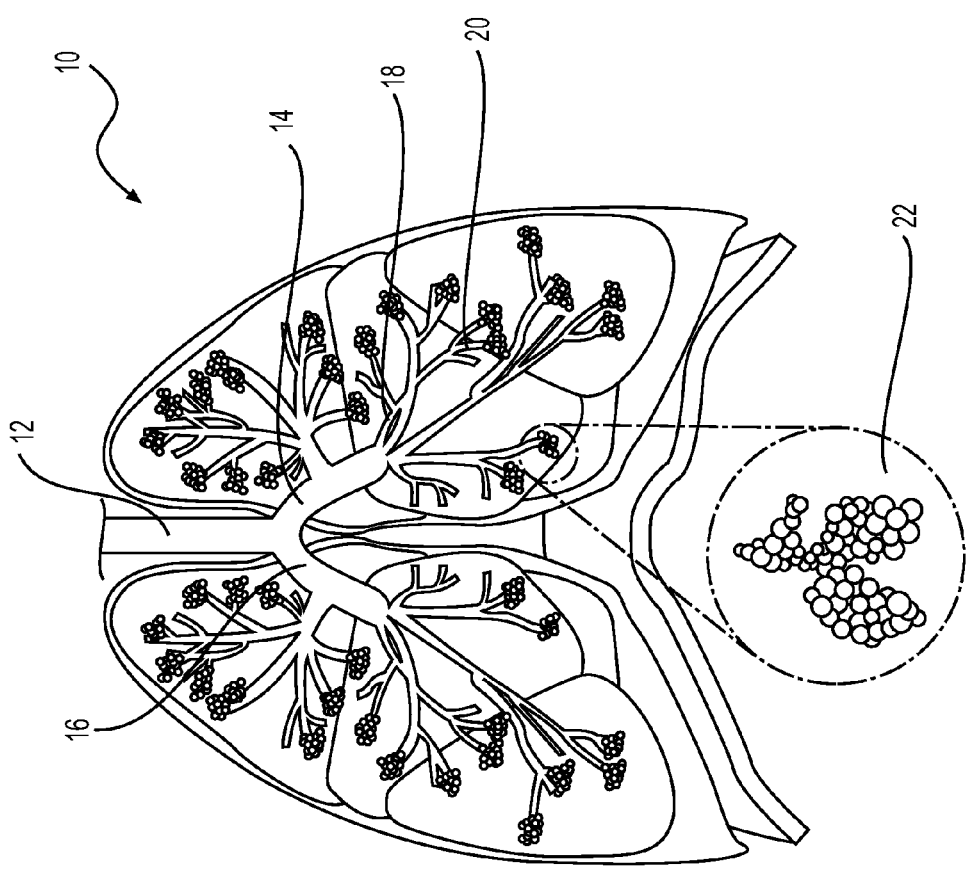
FIG. 1 is a diagrammatic view of healthy lungs.
Figure 2B:
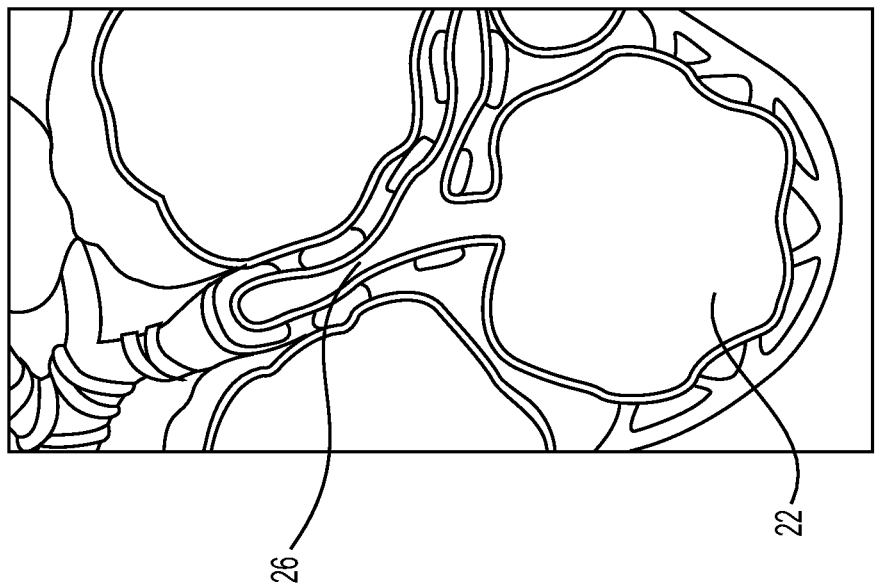
FIG. 2B is a diagrammatic illustration of an airway connected to an alveoli in the lung of FIG. 2A.
Figure 2A:
FIG. 2A illustrates a lung suffering from emphysema.
Figure 3A:
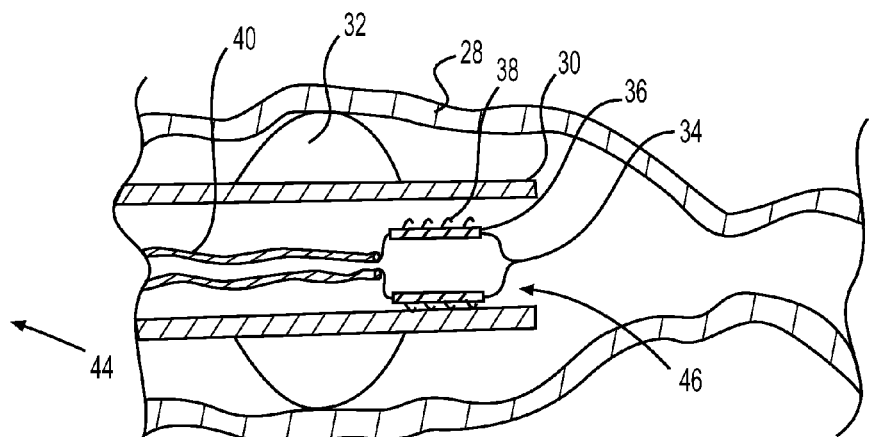
Figure 3B:
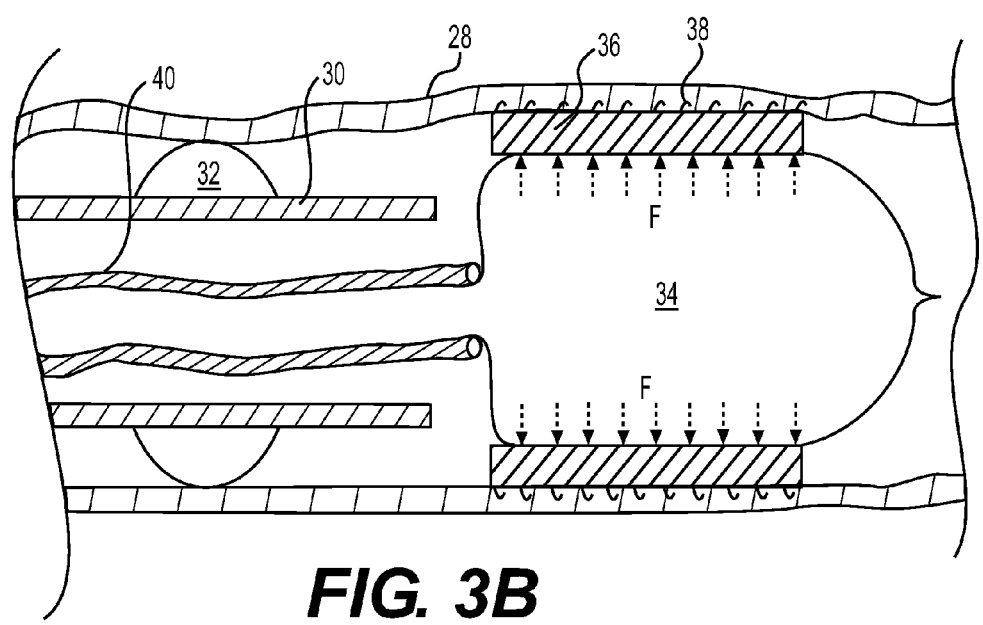

FIGS. 3A-3C depict the use of an exemplary embodiment of a device of the current disclosure to at least partially occlude an airway 28 in the lungs 10 (see FIG. 1) of a patient. In this disclosure, the term "airway" is used to refer to any of bronchi 18, bronchioles 20, and alveoli 22 in the lungs 10. The airway 28 may include diseased tissue which impairs the functioning of the lungs 10. A physician (or another user) may introduce a medical device, such as, for example, an introducer sheath 30 through the patient's airway 28 until a distal end of the sheath 30 reaches a target tissue area within airway 28. Sheath 30 may be introduced into airway 28 via any appropriate method. For example, sheath 30 may be deployed to the airway 28 independent of other medical devices, or be deployed to the airway 28 through a lumen of a bronchoscope, catheter, endoscope, or the like. While sheath 30 is referred to and described herein, it is to be understood that any luminal delivery device (e.g., endoscope, bronchoscope, catheter, etc.) may be used without departing from the scope of the disclosure. Sheath 30 may be sized to access the airway 28 (bronchi 18, bronchioles 20, and/or alveoli 22) without causing trauma to tissue. The sheath 30 may include a light source, such as, for example, a fiber optic cable or bundle, one or more light-emitting diodes (LED), and/or any other source of light sized for placement within a sheath 30. Additionally, sheath 30 may include a camera or vision system configured to receive images and relay them to a physician via a display device. The vision system may include an image sensor such as, for example, a CMOS or CCD image sensor.

Sheath 30 may optionally include a retention member such as, for example, balloon 32, configured to transition between an uninflated configuration (not shown) and an inflated configuration. Balloon 32 may expand within airway 28 so as to maintain the position of sheath 30 within the airway 28. Accordingly, balloon 32 may be configured to receive a source of inflation fluid through an inflation channel (not shown) in the sheath 30. In use, the sheath 30 may be in introduced into the airway 28 while the balloon is in an uninflated configuration. Upon reaching the target tissue area within airway 28, the balloon 32 may be transitioned to the inflated configuration (FIG. 3A) by directing inflation fluid into the balloon 32. Alternatively, any suitable expandable member (such as, for example, mechanical expansion cages, expandable foam members, hook and/or finger members, and expanding members activated by body heat or chemistry) may be used to maintain the position of the sheath 30 within the airway 28. Additionally or alternatively, balloon 32 (or any other expanding member) may include agents or drugs (such as, for example, antimicrobial agents, analgesics, anesthetics, etc.) to treat the tissue it comes into contact with. In some embodiments, sheath 30 may include an element or a mechanism configured to remove air from the balloon 32 distal to the balloon 32. In some embodiments, an air stream from the balloon 32 may be used to clear an airway 28 before occlusion.

The lumen, or working channel, of sheath 30 may be used to pass occluding devices into the airway 28. In the embodiment illustrated in FIGS. 3A-3C, the occluding device includes a stent-type scaffolding device (stent 36). As will be explained in more detail below, the stent 36 may expand in the airway 28 to engage tissue, and released to return to its collapsed position drawing the engaged tissue closed. In some embodiments, stent 36 (or sheath 30) may include other mechanisms to draw the engaged tissue closed. The stent 36 may be extended into the airway 28 using a balloon catheter 40 that is introduced into the airway 28 through the sheath 30. The catheter 40 may extend from a proximal end 44, positioned external to the airway 28, to a distal end 46 that extends into the airway 28 through the sheath 30. An inflatable balloon 34 may be coupled to the distal end 46 of the catheter. The balloon 34 may be configured to expand from an uninflated configuration (see FIG. 3A) to an inflated configuration (see FIG. 3B) when filled with air, saline, or another inflation fluid. The inflation fluid may be directed to the balloon 34 through the catheter 40. As will be explained in more detail below, the stent 36 may be introduced into the airway 28 positioned on the balloon 34, and may be configured to expand in the airway 28 with the balloon 34.

FIGS. 4A and 4B illustrate an exemplary stent 36 that may be used as an occluding device. Stent 36 may be a tubular member that is configured to radially expand from a first unexpanded configuration (FIG. 4A) to a second expanded configuration (FIG. 4B) upon application of an expanding force F (see FIG. 4B) that acts on an inner surface of the stent 36 in a radially outward direction. The tubular structure of the stent 36 may be formed by wires (or thin bands of material) that are configured to resiliently stretch when the stent 36 radially expands. When the expanding force F is removed, the stent 36 may substantially return to its unexpanded configuration. It is contemplated that the wires of the stent 36 may undergo some amount of plastic deformation as the stent 36 expands. Therefore, in some embodiments, the stent 36 may not completely return to its original unexpanded configuration when the expanding force F is removed. In some embodiments, the sheath 30 may include additional mechanisms to assist in drawing the stent 36 back to its unexpanded configuration and thereby occlude airway 28.

In some embodiments, the external surface of the stent 36 may include features such as, barbs or hooks 38. These hooks 38 may be configured to pierce tissue when the stent 36 is pressed against the tissue. As illustrated in FIG. 3A, the stent 36 may be disposed about the balloon 34 such that an inner surface of the stent 36 is in contact with the balloon 34. To position the stent 36 over the balloon 34, the stent 36 may be radially expanded and slipped over the uninflated (or slightly inflated) balloon 34 so that the stent 36 is snugly retained by the balloon 34. In some embodiments, the balloon 34 may be slightly inflated so that the stent 36 is securely retained by the balloon.

In use, the sheath 30 may be inserted into a patient and advanced to a desired airway 28 site. Before or after the sheath 30 is positioned at the desired site, the distal end 46 of the catheter 40 (with the stent 36 positioned on the balloon 34) may be inserted into the sheath 30 and advanced towards the airway 28. The balloon 34 at the distal end 46 of the catheter 40 may then be extended out of the sheath 30, and the inflation fluid directed into the balloon 34 to inflate it. The inflation fluid may be directed into the balloon 34 through a lumen of the catheter 40. Radiopaque markers (not shown) or other mechanisms (camera, etc.) on the sheath 30 and the catheter 40 may assist in correctly positioning them at the desired site.

As the balloon 34 inflates, the expanding balloon 34 pushes outwardly (that is, applies an expanding force F) on the stent 36, and causes the stent 36 to expand radially outwards along with the balloon 34. In some embodiments, as the stent 36 expands, the outer surface of the stent 36 pushes against the wall that defines an airway 28 lumen (airway wall) and forces the wall radially outward. As the stent 36 pushes on the airway wall, sharp edges of the wires that form the stent 36 penetrate and anchor the stent 36 on the wall tissue. In embodiments of the stent 36 with hooks 38 on its outer surface, the hooks 38 serve to anchor the stent 36 on the tissue. It is also contemplated that other structure and methods of anchoring may also be used.

The inflation fluid may then be directed out of the balloon 34 through the catheter 40 to deflate the balloon 34 and transform it to its uninflated configuration. The catheter 40 with the deflated balloon 34 may then be retracted out of the sheath 30. Deflating the balloon 34 removes the expanding force F from the stent 36 and allows the stent 36 to transform to its unexpanded configuration causing the stent walls to move radially inward. Since the external surface of the stent 36 is anchored on the airway wall, as the walls of the stent 36 move inward, the airway 28 wall in contact with the stent 36 also moves inward and at least partially occludes the airway 28. Over time, tissue grows over the stent 36 and prevents the reopening of the airway 28.

Although a specific embodiment of a stent 36 is described above, this is only exemplary. In general, any type of stent 36 that is capable of expanding to grasp the airway wall, and collapsing to pull the airway wall on to itself may be used. In some embodiments, a biocompatible adhesive may be applied to the external surface of the stent 36 to ensure that the airway wall attaches to the stent 36 surface when they come in contact. In some embodiments, the adhesive may be provided on an inside surface of stent 36. This adhesive may be applied in place of, or in addition to, the hooks 38. Further, in place of the balloon catheter 40, any suitable deployment device may be used to deploy the stent 36 at the desired airway 28 site. For instance, in some embodiments, an elongate member with radially extendable arms at its distal end may be used to deliver the stent 36 to an airway 36 and radially expand the stent 36 to snag the airway 28 wall.

Figure 5A:
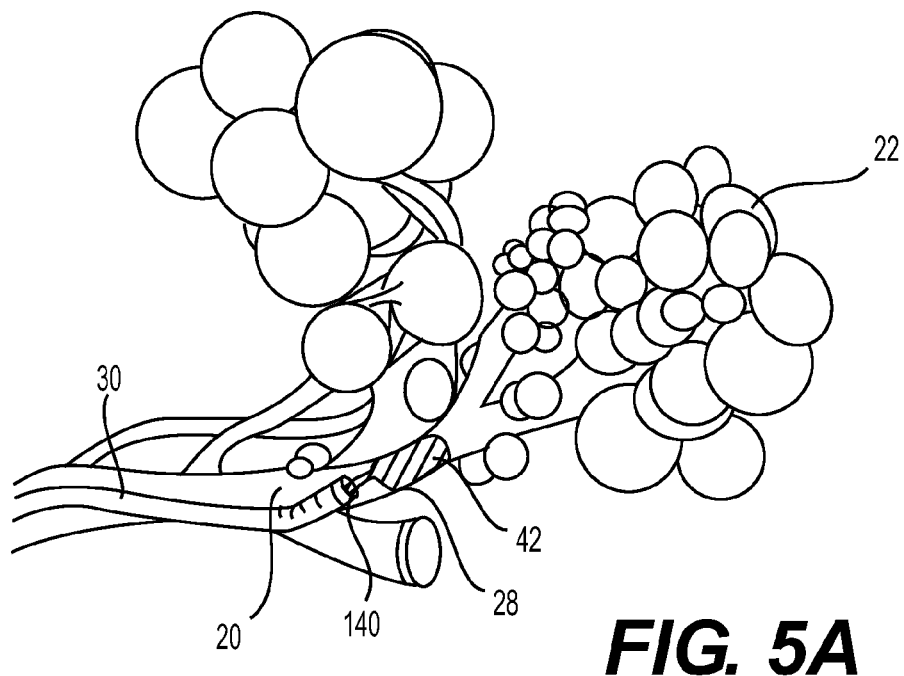
FIGS. 5A and 5B illustrate an exemplary embodiment of another device that may be used to occlude an airway in the lungs of FIG. 2B.
Figure 5B:
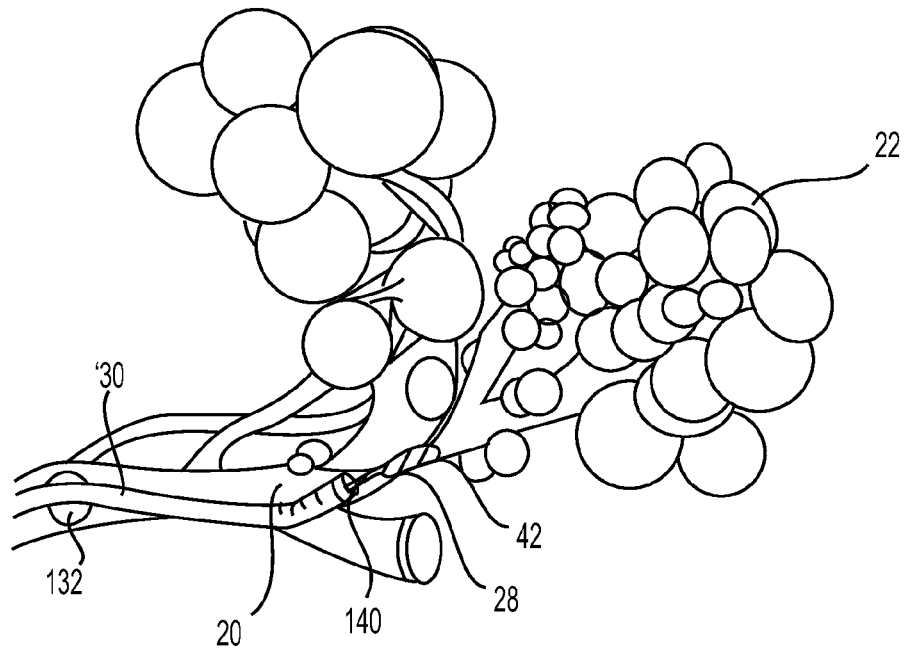

In some embodiments, in place of a stent, a balloon may be used to occlude an airway 28. FIGS. 5A and 5B illustrate an embodiment in which a balloon 42, with a muco-adhesive on its external surface, is introduced into an airway 28 attached to a catheter 140. At the airway 28, the balloon 42 is inflated to engage the wall of the airway 28 (FIG. 5A). As the balloon 42 pushes against the airway 28 wall, the airway 28 wall adheres to the balloon 42. The balloon 42 may now be deflated to draw the adhered wall of the airway 28 closed (FIG. 5B). The balloon 42 may be introduced into the airway 28 in a deflated state through a sheath 30. When the balloon 42 is suitably positioned at a desired airway 28 site, the balloon 42 is inflated with an inflation fluid to engage the external surface (with the adhesive) of the balloon 42 with the airway wall 28. The inflation fluid is then released from the balloon 42 to deflate the balloon 42. As the inflation fluid leaves the balloon 42, the balloon 42 collapses drawing the adhered airway wall shut. In some embodiments, the balloon 42 may now be released from the catheter 140 to leave the collapsed balloon 42 in place holding the airway wall closed.

In some embodiments, the balloon 42 may be configured to deflate slowly to gradually drag the opposite sides of the airway towards each other. In such embodiments, the balloon 42 may include one-way valves and/or pin holes to slowly release the inflation fluid therefrom. In some embodiments, the inflated balloon 42 (with a one-way valve that slows the release of the inflation fluid therefrom) may be released from the catheter 140 to occlude the airway 28. In such embodiments, as the balloon 42 deflates over time, the airway 28 wall will be gradually drawn shut.

Figure 6A:
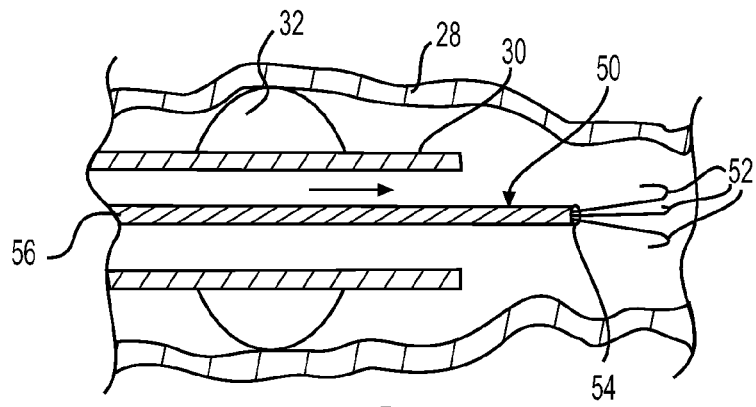
FIGS. 6A-6C illustrate an exemplary embodiment of a device used to capture airway tissue in the lungs of FIG. 2B.
Figure 6B:
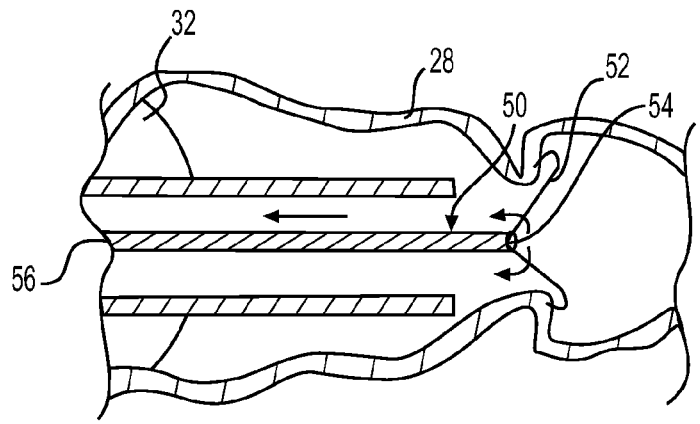
Figure 6C:
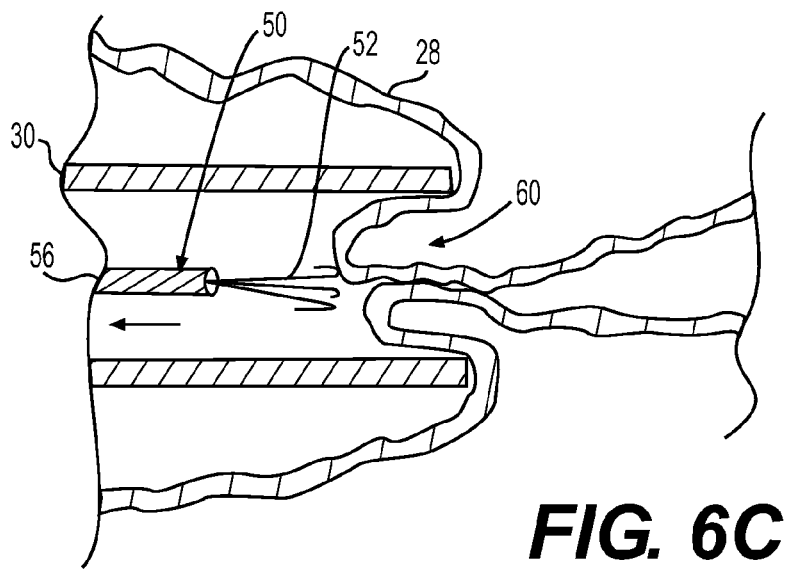

In some embodiments, a tool (such as a grasper) may be used to grasp airway wall and draw them towards each other to constrict, and thereby occlude, some or all of a diseased airway. In some such embodiments, a further mechanical or electrical treatment may be applied to the constricted airway to keep it permanently constricted. FIGS. 6A-6C illustrate an embodiment of a multi-pronged grasper 50 that is introduced into the airway 28 to capture and draw airway 28 tissue. Grasper 50 may include an elongate member 56 with a one or more prongs 52 at its distal end. The prongs 52 may have a hook-like shape or include a feature (barbs, protrusions, etc.) that is configured to snag tissue. The prongs 52 may be coupled to, or integrally formed (that is, formed as one continuous part from a same piece of material) with, the elongate member 56. In some embodiments, the prongs 52 may be coupled to the elongate member 56 through a pivot 54, and the prongs 52 may be configured to rotate/articulate about the pivot 54. The elongate member 56 and the prongs 52 may have any size and cross-sectional shape. The prongs 52 may be configured to transition between a first unextended configuration (FIG. 6A) and a second extended configuration (FIG. 6B) automatically, or in response to activation by a user from outside the patient's body. In the unextended configuration, the prongs 52 may extend substantially along, or parallel to, a longitudinal axis of the elongate member 56. In the extended configuration, the prongs 52 may extend substantially radial to, or angled away from, the elongate member 56.

In some embodiments, the prongs 52 may transform from their unextended to their extended configuration when the grasper 50 is extended into the airway 28. For instance, in some such embodiments, the grasper 50 may be deployed into the airway 28 through an outer sheath (sheath 30 or another sheath) or a cover that extends circumferentially about the prongs 52. When the grasper 50 is within the sheath, the wall of the sheath may push the prongs 52 radially inward to keep the prongs 52 in their unextended configuration. When the prongs 52 are extended out of the sheath (by pushing the grasper 50 distally relative to the sheath, or pulling the sheath proximally relative to the grasper 50), the prongs 52 may spring radially outwards to their extended configuration. Retracting the grasper 50 into the sheath may transition the prongs 52 back to their unextended configuration. In some embodiments, the prongs 52 may be made of a shape memory alloy to assist in their transformation between the unextended and extended configuration. It is also contemplated that, in some embodiments, the prongs 52 may transform from their unextended configuration within the sheath to their extended configuration outside the sheath in response to the conditions (such as, humidity, temperature, etc.) within the airway 28. In some embodiments, the prongs 52 may be transformed between their unextended and extended configurations by activating an activating member (trigger, etc.) positioned outside the body (that is, at the proximal end of the device). In such embodiments, wires or other link members (not shown) may extend from the prongs 52 to the proximal end to aid in their activation. It should be noted that, although the prongs 52 are shown as extending distally in the first unextended configuration (FIG. 6A), in some embodiments, the prongs 52 may extend in the proximal direction in the unextended configuration.

In use, the sheath 30 may be introduced into an airway 28 and advanced to a desired airway 28. Upon reaching a target tissue area within airway 28, a retention member, such as, for example, balloon 32, may be inflated to anchor, or otherwise retain, the sheath 30 in place within the airway 28. Such anchoring may prevent or inhibit accidental dislodging of the sheath 30 during a procedure. After anchoring the sheath 30 within the airway 28, a grasper 50 may be deployed through the working channel of sheath 30. That is, the grasper 50 may be inserted and advanced to a target tissue area in the airway 28 through the sheath 30. The elongate member 56 may be advanced distally past the distal-most end face of the sheath 30, so as to position the prongs 52 proximate the target tissue area. In some embodiments, the grasper 50 may include one or more radiopaque markers to assist in its proper positioning in the airway 28. After positioning the grasper 50 at a suitable target site, the prongs 52 may be moved to their deployed state (FIG. 6B). In the deployed state, the prongs 52 may extend radially outward from the elongate member 56 (like the ribs of an umbrella). The grasper 50 may then be retracted into the sheath 30. As the grasper 50 is retreated, the prongs 52 may snag/grasp or "catch" tissue that form the airway 28 wall, and pull the snagged airway together so as to bunch or fold the airway 28 in on itself, and drag the bunched or folded airway tissue (tissue folds 60) into the sheath 30 (FIG. 6C). In some embodiments, the prongs 52 may include sharp tips to pierce the tissue of the snagged airways 28 as the tissue is dragged into the sheath 30. Alternatively or additionally, in some embodiments, one or more of the prongs 52 may include suction members (or other features) to assist in snagging tissue. In such embodiments, one or more of the prongs 52 may include a channel (not shown) in fluid communication with a vacuum source (not shown).

In some embodiments, because of the reduced elasticity of the diseased airway, folding the airway 28 in on itself may permanently collapse and occlude the airway 28. In some embodiments, a treatment may be applied to the tissue folds 60 to permanently close the airway 28 and achieve lung volume reduction. The treatment may include a mechanical or an electrical treatment. Mechanical treatment may include applying an adhesive or a mechanical device (clips, rivets, etc.) to the tissue folds 60 to permanently occlude the airway 28. The electrical treatment may include cauterizing a portion of the tissue folds 60 to occlude the airway 28. For example, after forming the tissue folds 60, a cauterization member (not shown) may be delivered to the closed airway 28. The cauterization member may be used to deliver energy, e.g., heat, to the closed airway so as to seal (e.g., melt together) tissue at the target site. Optionally, after removal of cauterization member, an adhesive or a mechanical device may be deployed so as to maintain occlusion of airway 28.

Figure 7A:
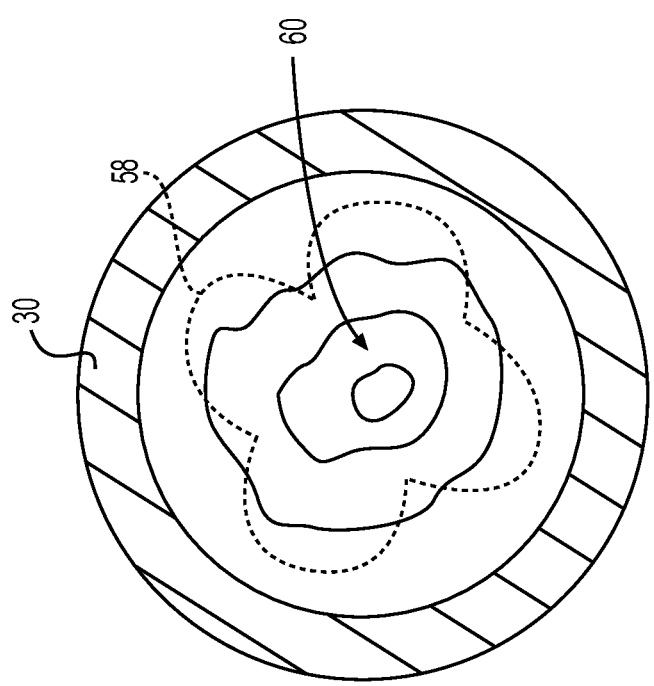
FIG. 7A is a diagrammatic illustration of an exemplary pattern of sutures that may be applied to the captured tissue of FIG. 6C to occlude the airway of FIG. 2B.

In some embodiments, a stapling device or a suturing device may be directed to the airway 28 to suture the tissue folds 60 together. Any type of suture device (such as, for example, Apollo Overstitch, or any of the devices described in U.S. Pat. Nos. 5,575,800, 7,766,925, or U.S. Patent Application Publication Nos. 2003/0130669, 2009/0177035, and 2010/0057109, etc. which are incorporated by reference herein) may be inserted into the airway and used to apply sutures to the tissue folds 60 in the airway 28. The stapling/suturing device may be inserted into the airway 28 through the sheath 30 to staple/suture the tissue folds 60. In some embodiments, as illustrated in FIG. 7A, the suturing device may be used to suture a path 58 around the tissue folds 60. After application of the sutures, the thread may be pulled to permanently close the airway 28 (for example, as in a purse-string suture). In some embodiments, a locking device may be applied to the tissue folds 60 after the suturing to keep the tissue folds 60 closed. Over time, the separate tissues that make up the tissue folds 60 may fuse together, to permanently occlude the airway 28. In some embodiments, the staples/sutures and the locking device may be bio-absorbable.

Figure 7B:
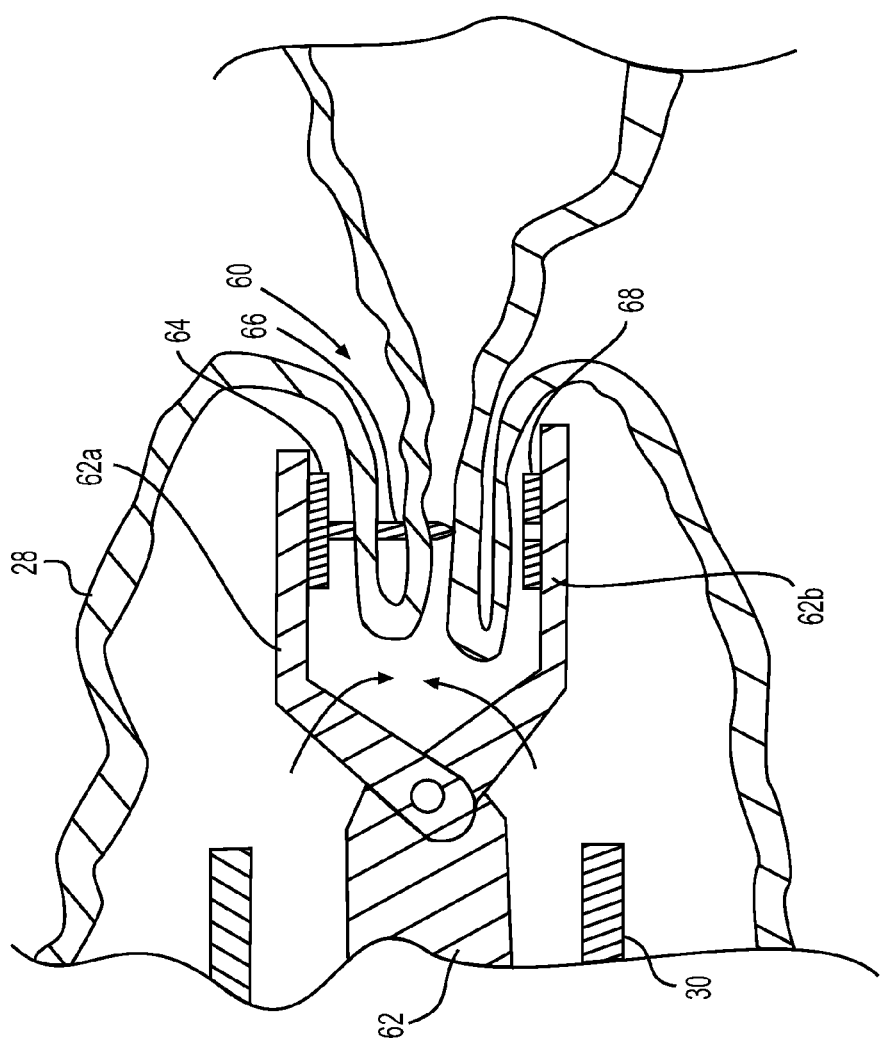
FIG. 7B illustrates an exemplary embodiment of a device that may be applied to the captured tissue of FIG. 6C to occlude the airway of FIG. 2B.

In some embodiments, as illustrated in FIG. 7B, tissue fasteners that includes, for example, a rivet 64 and a washer 68, may be directed to the airway 28 to apply to the tissue folds 60, and permanently close the airway 28. In such embodiments, after the tissue folds 60 are formed, the rivet 64 and the washer 68 may be introduced into the airway 28 using a deployment device 62. Any type of device that is adapted to apply the rivet 64 may be used as the deployment device 62. In the embodiment illustrated in FIG. 7B, the deployment device 62 may include an elongate member with a plurality of moveable jaws 62a, 62b at its distal end. The jaws 62a and 62b may be pivoted to each other and may be configured to rotate about the pivoting point from an open configuration to a closed configuration. In the open configuration, the distal ends of the jaws 62a, 62b are positioned away from each other, and in the closed configuration, the distal ends of the jaws 62a, 62b are positioned close to each other (see arrow in FIG. 7B). A rivet 64 may be positioned on one of the jaws 62a, and a washer 68 may be positioned on the other jaw 62b. The rivet 64 may include a pointed tip 66 that is oriented towards the washer 68. The rivet 64 and the washer 68 may be positioned on the jaws 62a, 62b such that they are adapted to separate from the respective jaws 62a, 62b upon the application of a small shear force (for example, using a light adhesive, or having frangible portions). Although a specific embodiment of a tissue fastener is discussed herein, it should be noted that any type of clips or other fastening devices that may be left behind in the airway may be used to occlude the airway 28.

In use, after formation of the tissue folds 60, the grasper 50 may be withdrawn and the deployment device 62 introduced into the airway 28 through the sheath 30. In some embodiments, a device having multiple lumens may be used to introduce both the grasper 50 and the deployment device 62 into the airway 28 at the same time. The deployment device 62 may include radiopaque markers (not shown) or other mechanisms to assist in appropriately positioning the deployment device 62 in the airway 28. After positioning the tissue folds 60 within the two jaws 62a, 62b, the jaws may be rotated to their closed configuration. As the jaws 62a, 62b rotate to their closed configuration, the pointed tip 66 of the rivet 64 pierces through the tissue folds 60 and enters the washer 68 to lock the tissue folds 60 together. After the rivet 64 engages with the washer 68, the deployment device 62 may be retracted into the sheath 30 to shear the rivet 64 and the washer 68 off the jaws 62a, 62b. In some embodiments, a separate trocar or a piercing device may be used to pierce the tissue prior to the application of the rivet 64. It should be emphasized that the deployment device 62 described above is only exemplary, and any suitable device may be used to apply the rivet 64 and the washer 68 on the tissue folds 60.

In some embodiments, in place of a rivet 64 and a washer 68, a biocompatible adhesive may be applied to the tissue folds 60 to adhere the separate tissue pieces together. It is also contemplated that tissue fastening devices such as staples, bands, clips, or any tissue fastening device disclosed in U.S. Patent Application Publication No. 2004/0044364 (which is incorporated by reference herein) may also be applied to the tissue folds 60 to occlude the airway 28. In some embodiments, the device used to permanently close the tissue folds 60 may be drug-eluting so as to promote proper tissue healing or sealing following a procedure. Although the exemplary devices and methods disclosed herein are described as being used to occlude an airway 28, in should be recognized that, in some embodiments, the airway 28 may not completely occlude. Instead, the airway 28 may only partially occlude.

While principles of the present disclosure are described herein with reference to illustrative embodiments for particular applications, it should be understood that the disclosure is not limited thereto. Rather, the devices and methods described herein may be employed to occlude any luminal tissue structure. Also, those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description. For example, while certain features have been described in connection with various embodiments, it is to be understood that any feature described in conjunction with any embodiment disclosed herein may be used with any other embodiment disclosed herein.

We claim:

1. A method of at least partially occluding an airway of a lung, comprising:
   deploying a catheter into the airway such that a balloon at a distal end of the catheter is positioned proximate a tissue wall that defines the airway;
   inflating the balloon to cause pressure to be applied on a portion of the tissue wall; and
   deflating the balloon to cause the portion of the tissue wall to be drawn radially inward to at least partially occlude the airway wherein a stent is circumferentially disposed about the balloon, the stent being configured to radially expand from a first unexpanded configuration to a second expanded configuration when the balloon inflates.

2. The method of claim 1, wherein inflating the balloon includes causing the stent to anchor to the portion of the tissue wall.

3. The method of claim 1, wherein deflating the balloon causes the stent to separate from the balloon and transform to a less expanded configuration.

4. The method of claim 3, wherein:
   the stent includes a first diameter in the first unexpanded configuration;
   the stent includes a second diameter greater than the first diameter in the second expanded configuration;
   expansion of the stent to the second expanded configuration causes plastic deformation of the stent; and
   the stent includes a third diameter between the first diameter and the second diameter in the less expanded configuration.

5. The method of claim 2, wherein the stent is anchored to the portion of the tissue wall via one or more hooks on an outer surface of the stent.

6. The method of claim 5, wherein the stent is anchored to the portion of the tissue wall via a biocompatible adhesive disposed on an outer surface of the stent.

7. The method of claim 2, wherein the stent is anchored to the portion of the tissue wall via a biocompatible adhesive disposed on an outer surface of the stent.

8. The method of claim 2, wherein the stent further includes a biocompatible adhesive on an inner surface of the stent to capture tissue.

9. The method of claim 1, wherein at least partially occluding the airway includes closing the airway at an occlusion site to prevent air from travelling through the occlusion site.

10. The method of claim 9, wherein the occlusion site is located proximal to an emphysematous portion of the lung.

11. The method of claim 10, wherein airflow is decreased to the emphysematous portion of the lung after deployment of the stent in the airway.

12. The method of claim 10, wherein airflow is increased through non-emphysematous portions of the lung after deployment of the stent in the airway.

13. The method of claim 1, further including an analgesic agent disposed on an outer surface of the balloon.

14. The method of claim 1, further including an antimicrobial agent disposed on an outer surface of the balloon.

15. A method of at least partially occluding an airway of a lung, comprising:
   deploying a catheter into the airway such that an expandable member at a distal end of the catheter is positioned proximate a tissue wall that defines the airway, wherein the tissue wall is located proximal to an emphysematous portion of the lung;
   expanding the expandable member to cause pressure to be applied on a portion of the tissue wall and causing a stent disposed radially outward of the expandable member to move from a first unexpanded configuration to a second expanded configuration to anchor the stent to the portion of the tissue wall, wherein the stent anchors to the portion of the tissue wall via a plurality of hooks and a biocompatible adhesive disposed on an outer surface of the stent; and
   retracting the expandable member to cause the stent to separate from the expandable member and transition from the second expanded configuration to a third configuration, causing the portion of the tissue wall to be drawn radially inward to at least partially occlude the airway at an occlusion site, wherein:
      at least partially occluding the airway restricts air from travelling through the occlusion site;
      the stent includes a first diameter in the first unexpanded configuration;
      the stent includes a second diameter greater than the first diameter in the second expanded configuration;
      expansion of the stent to the second expanded configuration causes plastic deformation of the stent;
      the stent includes a third diameter between the first diameter and the second diameter in the third configuration;
      airflow is decreased through the emphysematous portion of the lung after deployment of the stent in the airway; and
      airflow is increased through non-emphysematous portions of the lung after deployment of the stent in the airway.

16. The method of claim 15, wherein the expandable member is a balloon, an expansion cage, an expandable foam member, or an expandable member activated by heat.

17. The method of claim 15, wherein the stent further includes biocompatible adhesive on an inner surface of the stent to capture tissue.

18. A method of at least partially occluding an airway of a lung, comprising:
   deploying a catheter into the airway such that an expandable member at a distal end of the catheter is positioned proximate a tissue wall that defines the airway;
   expanding the expandable member to cause pressure to be applied on a portion of the tissue wall; and
   compressing the expandable member to cause the portion of the tissue wall to be drawn radially inward to at least partially occlude the airway wherein a stent is circumferentially disposed about the expandable member, the stent being configured to radially expand from a first unexpanded configuration to a second expanded configuration when the expandable member expands.

* * * * *